United States Patent [19]

Wang

[11] Patent Number: 4,618,475
[45] Date of Patent: Oct. 21, 1986

[54] REAGENT TEST DEVICE CONTAINING HYDROPHOBIC BARRIERS

[75] Inventor: Joseph Y. Wang, Elkhart, Ind.

[73] Assignee: Miles Laboratories, Inc., Elkhart, Ind.

[21] Appl. No.: 771,061

[22] Filed: Aug. 30, 1985

[51] Int. Cl.[4] .................... G01N 21/78; G01N 33/52
[52] U.S. Cl. ...................................... 422/56; 422/58; 435/805
[58] Field of Search ............................ 422/56, 57, 58; 436/169, 170; 435/805

[56] References Cited

U.S. PATENT DOCUMENTS

| | | | |
|---|---|---|---|
| 3,443,903 | 5/1969 | Haack et al. | 422/56 X |
| 3,723,064 | 3/1973 | Liotta | 422/56 X |
| 4,087,332 | 5/1978 | Hansen | 435/805 X |
| 4,160,008 | 7/1979 | Fenocketti et al. | 422/56 |
| 4,301,115 | 11/1981 | Rapkin et al. | 422/56 |
| 4,526,753 | 7/1985 | Boger et al. | 435/805 X |

FOREIGN PATENT DOCUMENTS 2655977  6/1978  Fed. Rep. of Germany ........ 422/56

Primary Examiner—Arnold Turk
Attorney, Agent, or Firm—Roger N. Coe

[57] ABSTRACT

Reagent test device are prepared in which reagent carrier matrices are separated from each other by hydrophobic barrier pads of identical height to the reagent carrier matrices such that liquid present in a reagent matrix material is retained therein and prevented from running over into another reagent matrix area present on the same test device.

8 Claims, 2 Drawing Figures ns set forth
REAGENT TEST DEVICE CONTAINING HYDROPHOBIC BARRIERS

FIELD OF THE INVENTION

The present invention relates to a reagent test device comprising reagent pads separated by a hydrophobic barrier pad attached to a substrate and, more particularly, to such test devices and a method of forming such test devices such that the reagent pads and the barrier pads have the same thickness. The alternating reagent pads and barrier pads mounted on a substrate prevent or minimize cross-contamination of reagents during use and also minimize damage to the reagent pads.

BACKGROUND OF THE INVENTION

The art of analytical chemistry has been greatly advanced since biochemistry began emerging as a primary scientific frontier, requiring increasingly sophisticated analytical methods and tools to solve problems. Likewise the medical profession has lent impetus to the growth of analytical chemistry, with its desiderata of both high precision and speed in obtaining results.

To satisfy the needs of the medical profession as well as other expanding technologies, such as the brewing industry, chemical manufacturing, etc., a myriad of analytical procedures, compositions and apparatus have evolved, including the so-called "dip-and-read" type reagent test device. Reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a reagent strip test device into a sample of body fluid, such as urine or blood, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular constituent in a test sample, but also an estimate of how much of the constituent is present. Such test devices provide the physician with a facile diagnostic tool as well as the ability to gage the extent of disease or of bodily malfunction.

Illustrative of such test devices currently in use are products available from the Ames Division of Miles Laboratories, Inc. under the trademarks CLINISTIX, MULTISTIX, KETOSTIX, N-MULTISTIX, DIASTIX, DEXTROSTIX, and others. Test devices such as these usually comprise one or more carrier matrices, such as absorbent paper, having incorporated therein a particular reagent or reactant system which manifests a detectable response, e.g., a color change, in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the test device with a sample is indicative of the presence of a particular constituent and/or its concentration in the sample. Some of these test devices and their reagent systems are set forth in U.S. Pat. Nos. 3,123,443; 3,212,855 and 3,814,668.

Thus, it is customary for reagent test devices to contain more than one reagent bearing carrier matrix, in which each reagent bearing carrier matrix is capable of detecting a particular constituent in a liquid sample. For example, a reagent test device could contain a reagent bearing carrier matrix responsive to glucose in urine and another matrix responsive to ketones, such as acetoacetate, which is spaced from, but adjacent to, the glucose responsive matrix. Such a product is marketed by the Ames Division of Miles Laboratories, Inc. under the trademark KETO-DIASTIX. Another reagent test device marketed by the Ames Division of Miles Laboratories, Inc., N-MULTISTIX, contains eight adjacent reagent incorporated matrices providing analytical measurement of pH, protein, glucose, ketones, bilirubin, occult blood, nitrite, and urobilinogen.

Despite the obvious, time-proven advantages of such multiple reagent test devices as these, misuse can result in misinformation. These multiple analysis tools comprise complex chemical and catalytic systems, each reagent matrix containing an unique reactive system, responsive to its particular analyte. Thus, it is possible, if the reagent test device is misused, for chemicals to be transported by the liquid sample being analyzed from one carrier matrix on the reagent test device to another. Should this happen it is possible for reagents from one carrier matrix to interfere with those of the other so contacted causing unreliable results. Although it is common in the reagent test device industry to provide detailed instructions on how this problem can be minimized, i.e., directions for properly manipulating the reagent test devices by blotting excess fluid, nevertheless ignorance or disregard of these instructions could permit reagents from one matrix to run over onto an adjacent one. Cross-contamination can result in false results. It is the prevention of this "runover" problem that the present invention is primarily directed.

The elimination of runover has been long sought after and the present discovery, which is the cumulation of an extensive research effort, provides a very effective solution to this problem. The present invention also minimizes damage caused by abrasion of the reagent pads during storage and use.

LITERATURE DISCUSSION

The patent literature is replete with accounts of myriad attempts at curtailing runover, the great bulk of the emphasis being directed to two basic concepts: the absorbance of runover liquid by bibulous layers placed beneath the reagent-bearing layers of reagent test devices; and the creation of hydrophobic barriers between the spaced matrices. The former has met with moderate success, whereas the latter approach has not.

Of the multilayer type reagent test devices, U.S. Pat. No. 4,160,008 describes a test device in which the carrier matrices containing reagent formulations are provided with absorbent underlayers which are separated therefrom by sample impervious barrier layers. Each matrix thus forms the upper layer of a laminate composite in which the barrier layer is disposed between the matrix and the absorbent base layer, the composite being fixed to a suitable support such as a plastic substrate. When the test device is dipped into the liquid sample the portion of sample which would otherwise runover from one matrix to another is largely absorbed into the underlayer of the latter through the exposed sides, the barrier layers of the composite preventing the absorbed runover from reaching the upper reagent layers.

U.S. Pat. No. 4,301,115 discloses and claims a test device comprising a base support member coated with a hydrophobic barrier layer to which a plurality of spaced apart reagent matrices are affixed. This approach virtually eliminates cross-contamination between adjacent reagent areas of multiple reagent test devices, but requires an extra step of applying hydrophobic material to the base support member of the reagent test device.

With respect to the development and use of barriers and/or barrier materials between reagent matrices, the patent literature is replete with teachings, which in theory, at least, would seem to overcome the runover problem.

U.S. Pat. No. 3,418,083 discloses an indicator-impregnated absorbent carrier matrix treated with wax, oil or similar "hydrophobic" agents. It is stated that when a sample of blood is placed on the resulting reagent test device, only colorless liquid components permeate it, the proteinaceous, colored blood components remain on the surface where they can be removed. Thus, it is taught that the liquid portion bearing the analysate permeates the reagent matrix pad and color interference is precluded.

Still another patent, U.S. Pat. No. 3,001,915, describes an absorbent paper reagent test device having spaced reagent-impregnated test areas for more than one sample component, each such area being separated from the other reagent-impregnated test area by a nonabsorbent barrier portion. The barrier is provided by impregnation of the paper strip with materials such as polystyrene, rosin, paraffin and various cellulose esters. The reagent strip is prepared, according to the reference, by impregnating a portion of the paper strip with a glucose sensitive reagent system. When dry, a solution of one or more of the barrier materials is applied to the paper adjacent a glucose sensitive portion. After further drying a protein sensitive reagent system is applied and the process is repeated with alternate applications of reagent and barrier solutions with drying steps inbetween.

Yet an earlier patent, U.S. Pat. No. 2,129,754, describes the impregnation of filter paper with paraffin wax whereby specific areas are left unimpregnated and these areas are treated with indicator systems for a particular analyte.

In U.S. Pat. No. 3,006,735 the concept of barrier material impregnated between reagent areas of a reagent test device is carried one step further by providing successive reagent areas responsive to different degrees of water hardness. Water repellent material, such as oils, waxes, silicones, and printer's varnish, is impregnated between these reagent test areas. Like the proceeding two patents this citation is restricted to paper or like bibulous material wherein reagent and barrier material alike are impregnated sequentially along the test device.

Despite lip service given by literature accounts to the elimination of runover, the fact remains that the problem continues to exist. The approaches disclosed in U.S. Pat. Nos. 4,160,008 and 4,301,115 have come the closest to eliminating the runover problem.

Prior attempts using wax, oils, silicones, and the like materials, have not curtailed runover to a clinically significant extent; and what modest advances have been made are more than offset by serious drawbacks inherent to such attempts. For example, applying hydrophobic material only at reagent area interstices embodies technical problems, especially when compared with the current techniques for manufacturing dip-and-read reagent test devices. Besides the obvious extra steps required by interstitial application, there is the danger of some of the hydrophobic material overlapping the reagent area thereby interfering with the paramount purpose of the reagent test device. Moreover, none of the substances taught by the prior art provides a suitable surface for adhesion.

Even if the above shortcomings were not prohibitive enough, the prior art hydrophobic substrates lack a degree of hydrophobicity required to prevent runover. They do not provide a sufficient contact angle to achieve the required hydrophobicity, nor do they provide a suitable surface for binding either the absorbent matrices or the reagents themselves, where they are coated directly on the substrate surface.

Unlike the prior efforts to establish a "barrier" between reagent areas of a test strip, the present invention does not attempt to create the barrier area by impregnating or coating a portion of the test strip. In fact, the barrier material of the present invention can be made from an entirely different type of material from that used to form the reagent pad. In any event, the construction of the test devices according to the invention permits the barrier material to be made entirely from hydrophobic material or be thoroughly saturated with hydrophobic ingredients prior to the formation of the test device to prevent any possible path through the barrier material from one reagent pad to another.

The present invention virtually eliminates cross-contamination between adjacent reagent areas of multiple reagent test device matrices. The results are truly incontrovertible and the success achieved in solving this problem represents an improvement over the use of a hydrophobic barrier layer, as described in U.S. Pat. No. 4,301,115. Moreover, the present invention has the advantages resulting in an excellent appearance of the final product in that the surface of the reagent test device is flat with no shadows between the reagent pads; the reagent test device is "stiffer" making the reagent test device easier to use and more accurate by reducing variations in instrument readings due to height variations; and the presence of the barrier pads of the same height as the reagent pads substantially reduces abrasion between reagent areas during transportation as well as materially reducing damage to the reagent pad areas during use.

SUMMARY OF THE INVENTION

An object of the present invention is to substantially eliminate runover problems by inserting a hydrophobic barrier between each reagent pad on a reagent test device.

Another object of the present invention is to eliminate abrasion between reagent test devices during transportation and minimize damage to the reagent pads during use by inserting a barrier area between the reagent pads which is of identical height to the reagent pads.

Still another object of the present invention is to provide a reagent test device with barrier materials inserted between reagent pads in which the barrier materials are constructed from different material from that of the reagent pads such that the barrier materials effectively eliminate runover between the reagent pads.

In accordance with the present invention, a reagent test device containing multiple reagent pads is formed with separate hydrophobic barrier pads separating each reagent pad and the barrier pads are maintained identical in height to the reagent pads so as to protect the reagent pads from abrasion or other damage during storage and use. The test devices of the present invention can be formed according to a preferred procedure by separately laminating hydrophobic reagent pads and hydrophobic barrier pads to a substrate while the substrate is maintained in a convex position such that when released from the curvature there is no gap or space between the reagent pads and the barrier pads.

DESCRIPTION OF THE DRAWINGS

Other and further objects, advantages and features of the invention will be apparent to those skilled in the art from the following detailed description thereof, taken in conjunction with the accompanying drawings, in which.

DESCRIPTION OF THE PREFERRED EMBODIMENTS

In accordance with the present invention reagent test devices are prepared having alternating reagent pads and barrier pads attached to a substrate in such fashion that there is no space between the pads and all of the pads are of the same height.

Figure 1:
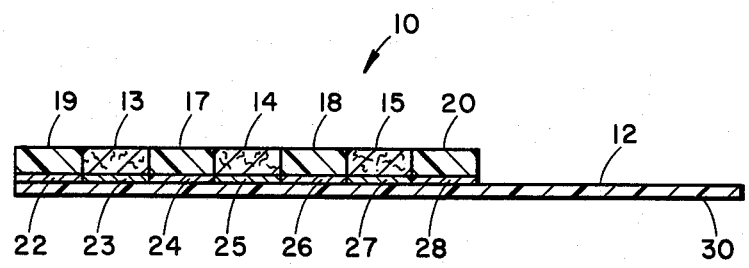
FIG. 1 is a schematic cross-sectional view of a test device in accordance with the present invention.

Referring to the drawings, FIG. 1 illustrates a test device 10 prepared in accordance with the present invention. Reagent test device 10 is composed of a substrate 12 containing three reagent pads 13, 14 and 15 separated by barrier pads 17 and 18. In addition, barrier pad 19 is shown on the end of test device 10 and another barrier pad 20 is shown on the opposite side of reagent pad 15 from barrier pad 18. The reagent pads 13–15 and the barrier pads 17–20 are separately bound to substrate 12 by means of a glue or adhesive 22–28 which connects the respective pads to substrate 12.

It will be observed that the resulting test device 10 provides a stiffer or more rigid test device than the conventional test device which does not have the barrier pads between the reagent pads. This feature facilitates the presentation to instruments for determining reflectance values and tends to improve the overall appearance and accuracy of the test device. Since the upper surface of the reagent area is flat there exists no clear demarcation line at the end of the reagent pads and no shadow exists. Moreover, the flat surface is very advantageous in that it minimizes abrasion between reagent pads during storage in a bottle or container, during transportation and in use. Conventional test devices, with reagent pads extending above a substrate surface, tend to expose the reagent pads to abrasion during storage and transit and subject the reagent pads to pressure when the exposed edges of the pad are caught on other pads or instruments used in the analysis procedure. Even if a reagent pad is not completely torn off a conventional reagent test device, it is important to minimize any contact which deforms or changes the surface or edges of a reagent pad since a slight deformation of the reagent pad surface can create substantial distortion in instrumental reflectance readings.

The barrier pads which separate reagent pads tend to be much more effective than prior art "barriers" placed between reagent test pads since the procedure for forming and applying the barrier pads is such that it permits all of the material used in a barrier pad to be hydrophobic. Preferably, the barrier pad is formed from a material which is completely different from that of the reagent pad. Thus, problems associated with attempts to employ the same material for both the impregnated reagent pad and for the impregnated barrier area are avoided. These problems include the problem of attempting to obtain substantial impregnation of hydrophobic barrier material and limit that impregnation to the barrier pad area such that there is no interference with the impregnated reagents. In the past it was often necessary to use hydrophilic material as the barrier material in order to obtain any impregnation.

The invention also makes it much easier to print a reagent test device with symbols or other designations and with "background color" on the barrier pads adjacent to the reagent pads, which symbols and color facilitate the accurate use of the resulting reagent test device.

Figure 2:
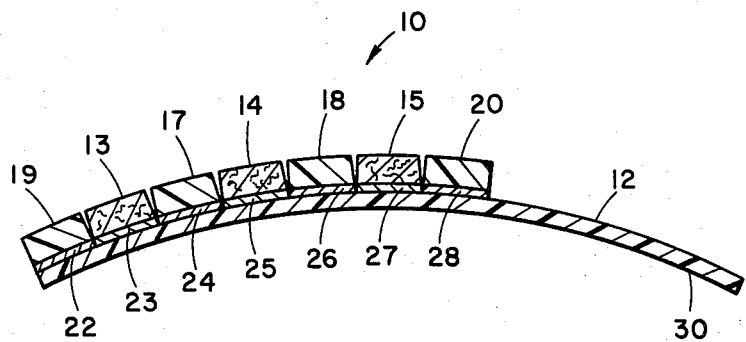
FIG. 2 is a schematic view of a test device in accordance with the present invention showing a preferred method of applying the reagent pads and barrier pads to the substrate.

FIG. 2 illustrates a preferred method of forming the reagent test device of FIG. 1. Since it is important to maintain the reagent pads and barrier pads adjacent to each other with no gaps in between (in physical contact) and since the reagent pads and barrier pads must be applied separately, either sequentially or concurrently, bending the substrate 12 slightly to form a convex surface facilitates applying the reagent pads and the barrier pads adjacent to each other such that when the flexible substrate 12 is released from its convex position the upper edges of the reagent pads and barrier pads come together leaving no space between them.

The substrate 12 can be formed from any suitable material including polystyrene, polyvinylchloride, polyethylene, polycarbonate, etc. Preferably the substrate 12 is flexible to facilitate manufacture in accordance with the procedure described above. Typically, the test device 10 will contain an elongated substrate such that one end 30 of substrate 12 can be used as a handle when the test device is dipped or contacted with test fluid being analyzed. The preferred material is Trycite, polystyrene, made by Dow Chemical Company.

The glue or adhesive material employed to bind the reagent pads and the barrier pads to substrate 12 can be any suitable material which is capable of bonding the pads to the substrate and readily adhering the different materials together. Double backed adhesive tape known a Double-Stick, available from the 3M Company, is preferred.

Reagent pads 13, 14 and 15 can be formed from any suitable material. U.S. Pat. No. 3,846,247 teaches the use of felt, porous ceramic material and woven or matted glass fibers. Additionally, U.S. Pat. No. 3,552,928 teaches the use of wood, cloth, sponge material and argillaceous substances. The use of synthetic resin fleeces in glass fiber felts as carrier matrix material is suggested in British Pat. No. 1,369,139. Another British Pat. No. 1,349,623, proposes the use of light permeable meshwork of thin filaments as a cover for an underlying paper matrix. Polyimide fibers are taught in French Pat. No. 2,170,397. Notwithstanding these suggestions, however, the material predominantly used in the art as carrier matrix for the reagent pads and those which are especially useful in the present invention are bibulous paper, such as filter paper, and porous hydrophilic film.

The reagent pad is normally impregnated with reagent material prior to bonding of the reagent pad to the substrate 12 using the adhesive material. Obviously, the reagents employed to impregnate reagent pads 13, 14 and 15 can and usually will be different.

The width of the barrier areas obviously can vary. Due to the effectiveness of the barrier areas these barrier pads do not need to be as wide as the reagent pads 13–15. This facilitates putting a larger number of reagent pads onto a reagent test device since obviously the number of reagent pads can be varied from one up to 10 or more. Typically, reagent test devices measure 8×0.5 centimeters and while these dimensions can be varied the practical aspects involved in handling and running several assays simultaneously dictates an upper limit on the number of reagent pads which it is feasible or practical to incorporate onto a particular test device.

The material employed for the barrier pad can be the same as that employed for the reagent pads but normally is not. The barrier pad can be impregnated with a suitable hydrophobic material including waxes, silicone materials and the like. Waxes which are especially useful in the present invention are thermoplastic, water repellent, smooth in texture, nontoxic and have freedom from objectionable odor or color. Major types of waxes which can be employed include natural waxes, such as animal wax, beeswax, spermaceti, lanolin, shellac wax; vegetable waxes, such as carnauba, candelilla, bayberry, sugar cane; mineral waxes, such as fossil or earth waxes, including ozocerite, ceresin, montan; and petroleum waxes, such as paraffin, microcrystalline, petrolatum; as well as synthetic waxes such as ethylenic polymers and polyolether-esters including Carbowax, sorbitol and chlorinated napthalenes such as Halowax and other hydrocarbon waxes. A preferred wax is the WW0404 wax from H. B. Fuller Company of Kalamazoo, Mich., which has the following characteristics: Melting point (ASTM D127) 82° C.±4%, hydrophobic, inert, bendable and not tacky when dry. The congeal point (ASTM D938) is 76° C.±4%, viscosity (Brookfield Thermocal) is 17.5 cps 93° C., and color (ASTM D1500) is 1.0 Saybolt.

The important consideration in the present invention, regardless of what material is employed to impregnate the barrier pads from the barrier is that the impregnation occurs prior to application of the barrier pad to substrate 12 such that impregnation occurs from all sides of the barrier material and this permits the barrier pad to be entirely impregnated with the hydrophobic material. One of the problems associated with prior art devices and especially with paper materials in which an attempt was made to create certain reagent areas and barrier areas in the same material by applying a coating or impregnating material to the surface of the material was that it was difficult to control and obtain a sharp line of demarcation between neighboring areas. Also it was difficult to assure that the material being impregnated was homogeneously impregnated with the desired impregnating material. Since the barrier pad is impregnated completely before it is associated with the test device substrate to form the ultimate test strip all of the barrier pad is hydrophobic.

In a preferred embodiment the barrier pad is formed from a hydrophobic, nonporous nonabsorbent material which is entirely different in character from the hydrophilic material typically used to form the reagent matrix area. Preferred materials include polystyrene, polyester, polyvinylfluoride and silica particles in an acrylic copolymer.

The width of the barrier pad 19 and 20 is not particularly critical, but the presence of these pads tends to aid in preventing abrasion or damage to the reagent pads 13 and 15, respectifully.

From the foregoing, it will be seen that this invention is well adapted to attain all of the ends and objects hereinabove set forth, together with other advantages which are obvious and which are inherent to the system. For example, the present invention has the advantage of convenience, simplicity, relatively inexpensiveness, positiveness, effectiveness, durability, accuracy and directness of action. The invention substantially overcomes problems associated with runover which have been continuing and long felt with multiple reagent test devices. The reagent strip has minimum curvature since the reagent strip is stiffer and the minimum curvature provides better handling for both visual and instrumental readings. With all of the pads at a uniform height the calibration of the system tends to be more reliable providing greater resolution in the readings. Moreover, the test devices have improved appearance since there is no shadow at any side of reagent pad and a clear color cutoff between the reagent pad and a barrier pad provides a strip with excellent appearance. A very important feature of the present invention is the minimization of damage to the reagent pads during storage, transportation and use since the barrier pads tend to protect the reagent pads. The uniform height of all the pads also facilitates improved visual readout by permitting the application of suitable background or negative colors as well as symbols on the barrier pads to facilitate reading of the reagent pads.

Obviously, many other modifications and variations of the invention as hereinbefore set forth can be made without departing from the spirit and scope thereof.

What is claimed is:

1. A reagent test device comprising multiple reagent carrier matrices attached in spaced relationship to one side of a substrate, with hydrophobic barrier pads of identical height to the reagent carrier matrices attached to the same side of the substrate between the reagent carrier matrices and in physical contact with the reagent carrier matrices to protect the reagent carrier matrices from abrasion and to prevent liquid runover between adjoining spaced carrier matrices.

2. The reagent test device of claim 1 in which the reagent carrier matrices and the barrier pads are attached to the substrate by means of adhesive.

3. The test device of claim 1 in which the reagent carrier matrix is filter paper.

4. The test device of claim 1 in which the reagent carrier matrix is porous hydrophilic film.

5. The test device of claim 1 in which the substrate is polystyrene.

6. The test device of claim 1 in which the substrate is polyvinylchloride.

7. The test device of claim 1 in which the barrier pad is polystyrene.

8. The test device of claim 1 in which the barrier pad is silica impregnated in an acrylic polymer.

* * * * *